United States Patent
Born et al.

[11] Patent Number: 6,093,788
[45] Date of Patent: Jul. 25, 2000

[54] PROCESS OF RECOVERING ε-CAPROLACTAM FROM PA-6 SYNTHESIS EXTRACT WATER

[75] Inventors: Claus Born, Ingelheim; Stefan Deibert, Offenbach/Main; Jürgen Schiwek, Hanau; Konrad Wolf, Frankfurt/Main, all of Germany

[73] Assignee: Lurgi Zimmer Aktiengesellschaft, Frankfurt Am Main, Germany

[21] Appl. No.: 09/169,531

[22] Filed: Oct. 9, 1998

[30] Foreign Application Priority Data

Dec. 2, 1997 [DE] Germany ............... 197 53 377

[51] Int. Cl.[7] .................... C08G 69/00; C08G 69/16; C08G 73/10
[52] U.S. Cl. .................... 528/310; 528/323; 528/335; 528/480; 528/488
[58] Field of Search .................... 528/310, 323, 528/480, 488

[56] References Cited

U.S. PATENT DOCUMENTS

| | | | |
|---|---|---|---|
| 4,053,457 | 10/1977 | Cordes et al. | 528/323 |
| 4,107,160 | 8/1978 | Dicoi et al. | 422/260 |
| 4,764,607 | 8/1988 | Balint et al. | 540/540 |
| 5,077,381 | 12/1991 | Dellinger | 528/323 |
| 5,169,870 | 12/1992 | Corbin et al. | 521/49.8 |
| 5,218,080 | 6/1993 | Dellinger | 528/323 |
| 5,241,066 | 8/1993 | Davis et al. | 540/540 |
| 5,294,707 | 3/1994 | Kotek | 540/540 |
| 5,556,890 | 9/1996 | Halderit et al. | 521/49.8 |
| 5,653,889 | 8/1997 | Buchanan | 264/37 |
| 5,777,067 | 7/1998 | Sato et al. | 528/310 |

FOREIGN PATENT DOCUMENTS

| | | |
|---|---|---|
| 0000397 | 7/1978 | European Pat. Off. . |
| 4316408 | 11/1994 | Germany . |

OTHER PUBLICATIONS

Riggert et al. ACHEMA '97: New developments in polymer and chemical fiber production. vol. 47, Sep. 1997, pp. 305–319.

*Primary Examiner*—P. Hampton-Hightower
*Attorney, Agent, or Firm*—McDonnell Boehnen Hulbert & Berghoff

[57] ABSTRACT

The invention comprises a process of producing ε-caprolactam from extract water of polycaprolactam obtained by hydrolytic polymerization, wherein (i) the extract water is concentrated by distillation of water, (ii) from the concentrated extract water from stage (i) an extract of ε-caprolactam and oligomers including dimers is obtained by separating an ε-caprolactam/water vapor mixture, (iii) the extract from stage (ii) is depolymerized in the presence of a catalyst and superheated steam, where a vapor mixture of ε-caprolactam and water is obtained, and (iv) from the ε-caprolactam/water vapor mixtures of process stages (ii) and (iii) ε-caprolactam with a dimer content of $\leq 0.2$ wt-% is obtained by distillation of water.

7 Claims, 1 Drawing Sheet

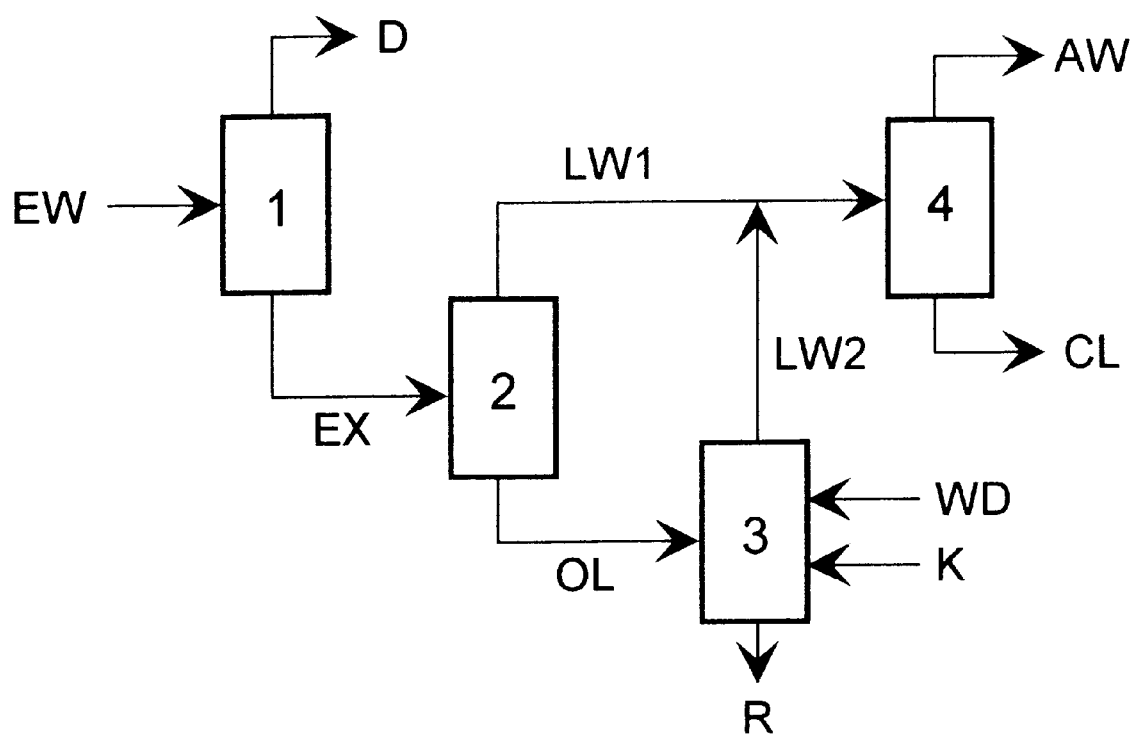

PROCESS OF RECOVERING ε-CAPROLACTAM FROM PA-6 SYNTHESIS EXTRACT WATER

BACKGROUND OF THE INVENTION

1. Field of the Invention

The present invention relates to a process of recovering ε-caprolactam from the extract water of polycaprolactam produced by hydrolytic polymerization.

SUMMARY OF THE RELATED ART

The hydrolytic synthesis of polycaprolactam (PA-6) from the monomeric ε-caprolactam results in up to 15 wt-% of unreacted monomeric ε-caprolactam and its oligomers remaining in the polymer, depending on the reaction conditions. Since the vacuum de-monomerization of the PA-6 melt—either in falling films or in disk reactors—does not reduce the content of monomers and oligomers in the polymer to an acceptably low level required for spinning purposes, the continuous or discontinuous extraction of PA-6 chips with hot water on an industrial scale has gained acceptance. By means of this process, monomer and oligomer contents of <0.5 wt-% in the PA-6 chip are achieved.

For economic reasons, the aqueous extract solutions are processed so that the valuable substances contained therein can be recycled for use in the synthesis of polycaprolactam. After a simple concentration of the extract water by evaporation, the cyclic dimers and other oligomers (as well as monomeric ε-caprolactam) remain in the recovered caprolactam.

The recirculation of these oligomers to the PA-6 production process negatively affects the conversion of raw material, and in the case of an incomplete extraction, can potentially lead to a deterioration of the PA-6 product. This is because the oligomers, in particular the cyclic dimer, are involved in the PA-6 chain formation only to a small degree due to their high stability and related chemical inactivity. The cyclic dimer is enriched by repeated extraction and recirculation cycles in the melt and in the extract solutions.

Patent DE 2501348 B describes the concentration of the extract water to an extract content of more than 90 wt-% with subsequent direct introduction into the polymerization stage both with and without the addition of fresh caprolactam. In accordance with Patent EP 0000397 B, extract water concentrated to a maximum extract content of 60 wt-% may also be recirculated to the polymerization reaction. In both cases, the extract solutions—with or without addition of fresh caprolactam—are heated before metering into the head of a VK-tube to ensure that the high-melting and weakly soluble cyclic dimer of the 6-caprolactam remains in solution under these conditions so that no clogging of the lines or the like will occur. This does not sufficiently ensure the splitting of the cyclic dimer, which is necessary for the subsequent incorporation in the polymer chain.

Patent application EP 0771834 A describes the concentration of the extract water with subsequent partial ring opening reaction of the oligomers to form linear condensable compounds under reaction conditions of 230° C.–300° C. at defined pressures, which are maintained for up to 10 h. The extracts thus treated are subsequently polymerized in a reactor together with fresh caprolactam, where water may be present in concentrations of up to 10 wt-%. According to U.S. Pat. No. 5,218,080, the hydrolytic decomposition of dimers of the concentrated extract is performed under pressure at 220–290° C. for 2 to 6 h, where the extract thus obtained with a dimer content of about 1.3 wt-% is directly added to the fresh caprolactam in an amount of up to 10 wt-%. In view of an increasing rise in capacity of continuously operated plants for the hydrolytic polymerization of caprolactam, the profitability of this process and the level of the remaining content of dimers in the extract thus processed must still be improved.

Furthermore, a process in which the extract water is concentrated to about 80 wt-% ε-caprolactam/oligomers and then polymerized to PA-6 in a second, separate polymerization line without further addition of fresh caprolactam has been reported in *Chemical Fibers International* 47, 316 (1997). A disadvantage of this process is the high investment costs for the complete second polymerization line, in which a reactivation of dimers is effected under polymerization conditions differing from those of the process of polymerizing fresh caprolactam in the first line. The increased water content deteriorates the economy of this second line. Due to the altered product quality, cutter, extraction and drying must also be additional elements of this second line.

Other processes involving a separate processing of the oligomers and cyclic dimers contained in the extract water require a separation of these constituents from the extract water. U.S. 5,653,889 describes a filtration technique for separating the oligomers from the process water of the PA-6 granulation stage. This filtration technique cannot be easily applied to separation and processing of oligomers from an aqueous extract solution of ≦15 wt-% that also contains monomeric ε-caprolactam.

For processing the oligomers, a process in accordance with U.S. 4,107,160 can be used, where—in addition to PA-6 solid wastes—the oligomers are depolymerized in the presence of a catalyst and superheated steam. After a subsequent concentration, about 50 wt-% aqueous ε-caprolactam solution can be obtained that, according to patent application DE 43 16 408 A, is then filtrated and evaporated after a refining stage with permanganates and a treatment with activated carbon. After a fine distillation, the pure caprolactam obtained may be recirculated to a PA-6 production process. This complex process, which delivers high quality recovered caprolactam, is accompanied by increased costs due to consumption of materials such as permanganate and activated carbon, numerous process stages, and correspondingly high energy consumption.

The alternatively possibility of disposing the oligomers isolated from the extract water dramatically reduces the yield of raw material and thus does not present an economically feasible procedure, particularly with increasing plant capacities.

SUMMARY OF THE INVENTION

The present invention provides a process for recovery of ε-caprolactam with a low oligomer content and a dimer content of ≦0.2 wt-% (based on ε-caprolactam) from the extract water of a hydrolytic PA-6 polymerization and its recirculation to the PA-6 production process without significantly affecting the PA-6 production process or the PA-6 product quality. The inventive process is further characterized by a high profitability. The need for a complete PA-6 recycling plant, with high investment and operation costs, is thereby eliminated.

The process generally comprises (i) concentrating the extract water of hydrolytic PA-6 polymerization reaction to at least 70 wt-% solids, (ii) separating an ε-caprolactam/water vapor mixture from the concentrated extract water, (iii) depolymerizing the extract from stage (ii) in the presence of a catalyst and superheated steam, and distilling the ε-caprolactam/water vapor mixtures from stages (ii) and (iii).

The foregoing merely summarizes certain aspects of the invention and is not intended, nor should it be construed, as limiting the invention, which is described in greater detail below.

BRIEF DESCRIPTION OF THE DRAWING

The FIGURE displays of schematic depiction of the process according to the invention.

DETAILED DESCRIPTION OF THE PREFERRED EMBODIMENTS

More particularly, the present invention provides a process for recovery of ε-caprolactam from the extract water of a hydrolytic PA-6 polymerization, the process comprising (i) concentrating the extract water of a hydrolytic PA-6 polymerization reaction by means of a single- or multi-stage distillation to a solids content of at least 70 wt-%

(ii) separating an ε-caprolactam/water vapor mixture from the concentrated extract water from stage (i) to yield an extract containing 33 to 67 wt-% ε-caprolactam and 67 to 33 wt-% oligomers (including dimers) (wherein wt-% ε-caprolactam+wt-% oligomers=100), (iii) depolymerizing the extract from stage (ii) in the presence of a catalyst and superheated steam to yield a vapor mixture of 16 to 33 wt-% ε-caprolactam and 84 to 67 wt-% water (wherein wt-% ε-caprolactam+wt-% water=100), and (iv) distilling the ε-caprolactam/water vapor mixtures of process stages (ii) and (iii) in a single- or multi-stage process to yield ε-caprolactam with a water content of not more than 15 wt-% and a dimer content of not more than 0.2 wt-%.

In an alternative embodiment of the process, the ε-caprolactam/water vapor mixture from stage (ii) is condensed before entering stage (iv). The ε-caprolactam/water vapor mixture from stage (iii) optionally can likewise be condensed. Both ε-caprolactam/water vapor mixtures can also be combined first and then condensed together.

It was surprisingly found that the processing of an extract water containing dimers and oligomers from the PA-6 production process in the oligomer separation in stage (ii) and the oligomer splitting in stage (iii) with subsequent concentration of the ε-caprolactam/water vapor mixtures in stage (iv) is sufficient to achieve a quality of the recovered caprolactam that allows adding any amount of recirculated caprolactam to fresh caprolactam or exclusively utilizing the recovered caprolactam as raw material for the production of polycaprolactam without noting a significant affect on the process or product quality as compared to the process of producing PA-6 from 100 wt-% fresh caprolactam.

The ε-caprolactam obtained in stage (iv) is characterized by a water content of ≦15 wt-%, preferably ≦4 wt-%, and a dimer content ≦0.2 wt-%, preferably ≦0.05 wt-%. The yield of recovered caprolactam is at least 99 wt-%, based on the sum of ε-caprolactam, oligomers, and dimers in the extract water.

The inventive process uses aqueous extracts as they are obtained from a single- or multistage, continuous or discontinuous extraction of polycaprolactam. Other aqueous solutions containing ε-caprolactam, which are obtained, for instance, from the granulation stage or by condensation of vapors from the polymerization, can also be processed unless they contain disturbing impurities.

As is schematically displayed in FIG. 1, the extract water EW is separated in the evaporation 1 into the top fraction D and the bottom fraction EX. The evaporation may be effected in a single- or multi-stage distillation plant, where natural circulation or forced-circulation evaporators, falling-film evaporators, thin-film or Roberts evaporators etc. are preferably operated in combination with a rectification column, such as a plate column, packed column or packing column, etc. The single-stage version may be operated at pressures of 100 to 200 kPa (absolute) and at bottom temperatures of 100 to 160° C. The operation of two- to four-stage plants may be effected at pressures of 20 to 200 kPa (absolute) and at bottom temperatures of 60 to 160° C. with parallel or countercurrent connected evaporators. The water obtained in the top fraction D contains a maximum of 0.1 wt-% ε-caprolactam and can be utilized for another extraction of unextracted polycaprolactam. In the bottom fraction EX the concentrated extract is obtained with a solids content ≧70 wt-% (preferably ≧90 wt-%) and subsequently transferred to the oligomer separation 2.

In the oligomer separation stage 2, the bottom fraction EX is evaporated to such an extent that the bottom product OL is an extract composition of 33 to 67 wt-% ε-caprolactam and 67 to 33 wt-% oligomers, preferably about 50 wt-% ε-caprolactam and about 50 wt-% oligomers. The evaporation may be effected in Roberts or thin-film evaporators at pressures of 5 to 100 kPa (absolute) and temperatures of 150 to 250° C. The top product LW1, which consists of ε-caprolactam and the residual water from the fraction EX, may be supplied as vapor or, after a corresponding condensation in a shell-and-tube, plate, U-tube or coil condenser etc., in liquid form as lactam water LW1 to the concentration 4. This condensate preferably contains ≧50 wt-%, more preferably ≧85 wt-%, ε-caprolactam.

In the oligomer depolymerization 3, the oligomers including the cyclic dimers of the ε-caprolactam/oligomer stream OL are depolymerized to the stage of amino caproic acid or ε-caprolactam under the influence of a depolymerization catalyst K, for instance phosphoric acid, and of steam WD super-heated to 250 to 450° C., preferably 340 to 380° C. As to the execution of the depolymerization stage, reference is made to U.S. Pat. No. 4,107,160 and DE 4316408 A. The depolymerization reactor may be operated with or without a condenser, and the use of a rectification column as a plate column, a packed or packing column, etc., is also possible. The bottom temperature is at least 220° C., preferably at least 240° C. at atmospheric pressure. The depolymerization may, however, also be effected under a vacuum or at an excess pressure and at temperatures correspondingly adapted to the pressure. Due to the use of a depolymerization catalyst K, a residue R is obtained in process stage 3, which residue is discharged regularly. The escaping mixture of vapors with an ε-caprolactam content of 16 to 33 wt-%, preferably about 25 wt-%, will be transferred to the concentration 4 as vapor or, after a corresponding condensation, in the liquid form as lactam water LW2. When a rectification column is used, a partial concentration is effected together with the condensation, where the condensate is preferably adjusted to an ε-caprolactam content of ≧30 wt-%, more preferably ≧60 wt-%.

In the concentration 4, the lactam water product streams LW1 and LW2 are concentrated in a single- or multi-stage distillation, where the ε-caprolactam CL is obtained as bottom product with a residual water content ≦15 wt-%, preferably ≦4 wt-%, and a dimer content ≦0.2 wt-%, preferably ≦0.05 wt-%, based on ε-caprolactam, while the waste water AW is discharged from the top. For the technical execution, a single- or multi-stage distillation plant may be used, where natural-circulation and forced-circulation evaporators, falling-film evaporators, thin-film or Roberts evaporators etc. are operated in combination with a rectification column, such as a column as a plate column, a packed or packing column, etc., at bottom temperatures of 30 to 160° C. and pressures of 1 to 200 kPa (absolute). In the case of a multi-stage plant, the evaporators may be operated in a parallel or countercurrent connection.

As a result of the treatment of the extract water in process stages 1 to 4, the quality of the $\epsilon$-caprolactam obtained is sufficient to permit subjecting it as it is to hydrolytic polymerization to produce polycaprolactam without any significant losses of quality in the polycaprolactam. With a continuous operation, the recovery rate of $\epsilon$-caprolactam from the extract is at least 97 wt-%, preferably at least 99 wt-%, based on the sum of $\epsilon$-caprolactam, oligomers, and dimers in the extract water.

EXAMPLE

Extract water containing 8.3 wt-% $\epsilon$-caprolactam, 1.2 wt-% oligomers, and 0.4 wt-% dimers from a PA-6 extraction was first concentrated in a fractional distillation plant at a bottom temperature of 40° C. and a pressure of 6 kPa (absolute) to a solids content of 90 wt-%, where the water withdrawn was used for another PA-6 extraction. Upon distillation of the residual water-starting with a bottom temperature of 40° C. and a pressure of 6 kPa (absolute), $\epsilon$-caprolactam could be withdrawn from the top at a bottom temperature of 125° C. and a pressure of 0.6 kPa (absolute) to such an extent that in the distillation boiler a bottom product consisting of 50 wt-% oligomers and 50 wt-% $\epsilon$-caprolactam remained (oligomer separation). The water distilled off and the $\epsilon$-caprolactam were condensed, and the condensate temporarily stored. Upon transfer of the bottom product, consisting of 50 wt-% oligomers and 50 wt-% $\epsilon$-caprolactam, into a PA-6 depolymerization reactor, depolymerization was effected at a bottom temperature of about 250° C. and atmospheric pressure by adding 15 wt-% phosphoric acid (85 wt-%) and a steam flow of 300° C. and 10 ml/(min·kg).

The condensed $\epsilon$-caprolactam/water vapor mixture escaping from the depolymerization was evaporated in a distillation plant at a bottom temperature of 40° C. and a pressure of 6 kPa (absolute) to an $\epsilon$-caprolactam content of 70 wt-%. Upon combining this condensate with the temporarily stored $\epsilon$-caprolactam/water condensate from the process stage of the oligomer separation, the further concentration of the total condensate was effected in the distillation plant at a bottom temperature of 40° C. and a pressure of 6 kPa (absolute) to a residual water content of 5 wt-%.

The analysis of the 95 wt-% aqueous $\epsilon$-caprolactam sample that was left in the distillation boiler revealed a dimer content of 0.04 wt-%, based on $\epsilon$-caprolactam.

The analysis of the extract water composition and of the dimer content in the $\epsilon$-caprolactam/water mixture was effected by means of HPLC.

We claim:

1. A process of producing $\epsilon$-caprolactam from extract water of polycaprolactam obtained by hydrolytic polymerization, the process comprising
    i) concentrating the extract water by means of single- or multi-stage distillation to a solids content of at least 70 wt-%,
    ii) separating an $\epsilon$-caprolactam/water vapor mixture from the concentrated extract water from stage (i) to produce an extract containing 33 to 67 wt-% $\epsilon$-caprolactam and 67 to 33 wt-% oligomers and dimers,
    iii) depolymerizing the extract from stage (ii) in the presence of a catalyst and superheated steam to produce a vapor mixture of 16 to 33 wt-% $\epsilon$-caprolactam and 84 to 67 wt-% water, and
    iv) subjecting the $\epsilon$-caprolactam/water vapor mixtures of process stages (ii) and (iii) to single- or multi-stage distillation to produce $\epsilon$-caprolactam with a water content of not more than 15 wt-% and a dimer content of not more than 0.2 wt-%.

2. The process as claimed in claim 1, characterized in that the $\epsilon$-caprolactam/water vapor mixture from stage (ii) and/or from stage (iii) is condensed before entering stage (iv).

3. The process according to claim 1, wherein phosphoric acid is used as catalyst in stage (iii).

4. The process according to claim 1, wherein the superheated steam of stage (iii) has a temperature in the range from 250 to 450° C.

5. The process according to claim 1, wherein in stage (i) the extract water is concentrated to a solids content of at least 90 wt-%.

6. The process according to claim 1, wherein the $\epsilon$-caprolactam obtained in stage (iv) has a water content of not more than 4 wt-% and a dimer content of not more than 0.05 wt-%.

7. The process according to claim 1, wherein the $\epsilon$-caprolactam obtained in stage (iv) is subjected, alone or mixed with fresh $\epsilon$-caprolactam, to a hydrolytic polymerization to obtain polycaprolactam.

* * * * *